United States Patent [19]
Amburn

[11] 3,991,714
[45] Nov. 16, 1976

[54] METHOD OF MAGNETICALLY TREATING EGGS AND ANIMAL SEMEN

[76] Inventor: Raymond D. Amburn, 8325 Riverland Drive (Bldg. 6 No. 1), Sterling Heights, Mich. 48078

[22] Filed: July 21, 1975

[21] Appl. No.: 597,844

Related U.S. Application Data

[62] Division of Ser. No. 403,571, Oct. 4, 1973, Pat. No. 3,910,233.

[52] U.S. Cl. .................................................. 119/1
[51] Int. Cl.² ......................................... A01K 45/00
[58] Field of Search ...................... 119/1; 128/1.5; 195/1.7, 118; 324/34 R; 21/54 R; 426/237, 241, 298

[56] References Cited
UNITED STATES PATENTS 3,658,051   4/1972   MacLean .......................... 128/1.5

*Primary Examiner*—Hugh R. Chamblee
*Attorney, Agent, or Firm*—Reising, Ethington, Barnard, Perry & Brooks

[57] ABSTRACT

A method of treating semen from male fowl to increase the production of fertile eggs by female fowl inseminated with the treated semen by exposing the semen to a magnetic field of predetermined intensity and for a predetermined period of time. The semen so treated increases the number of fertile eggs produced by the female fowl inseminated with the treated semen. The invention also includes a method for treating fertile eggs to increase the hatch rate and the rate of growth of fowl hatched from the treated eggs. The eggs are treated by placing the eggs in a magnetic field of predetermined intensity to expose the eggs to the magnetic field and then removing the eggs from the field after a predetermined period of time. Preferably, the magnetic treatment of the eggs is done prior to incubation. The invention also includes apparatus for magnetically treating eggs, vials of animal semen, or other fragile articles, such apparatus including a magnet for producing a magnetic field and supporting means of soft resilient material extending through the magnetic field for supporting articles moving through the magnetic field. The apparatus may also include means for revolving the eggs, vials of semen, or other articles, as they move through the magnetic field to constantly change the orientation of the article with respect to the magnetic field during the time that the article is being treated in the magnetic field.

11 Claims, 5 Drawing Figures

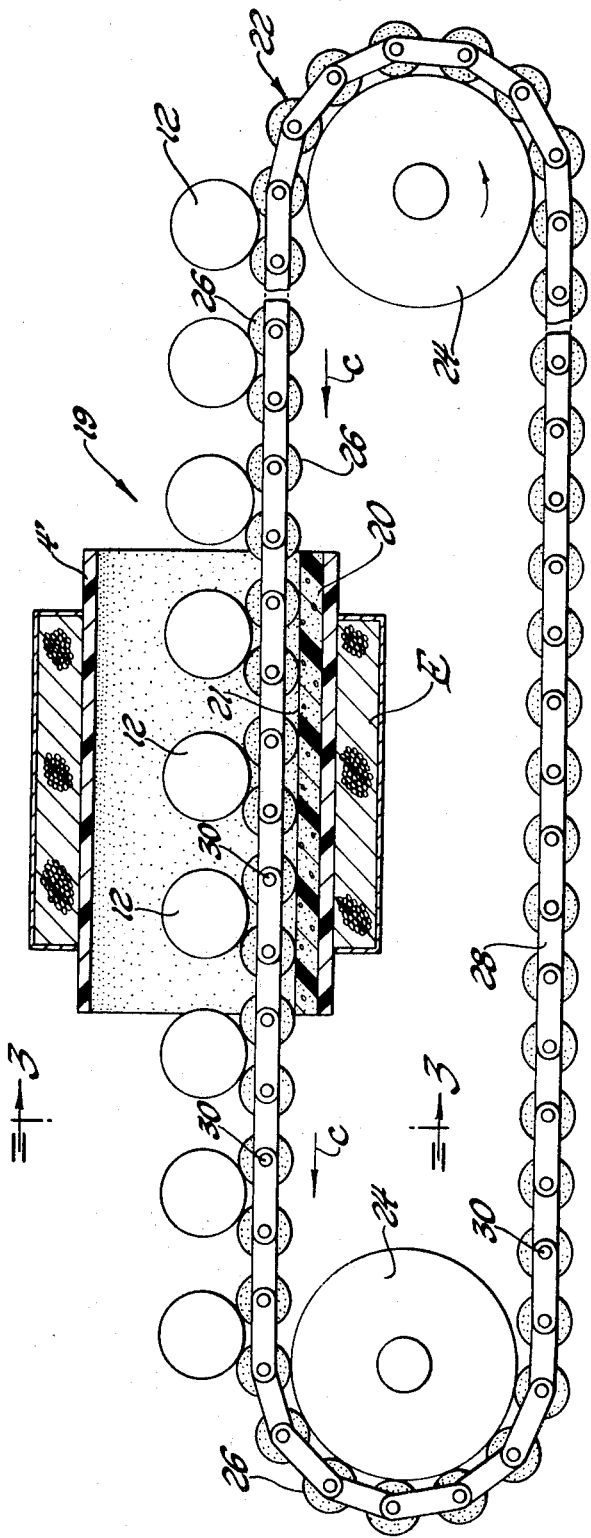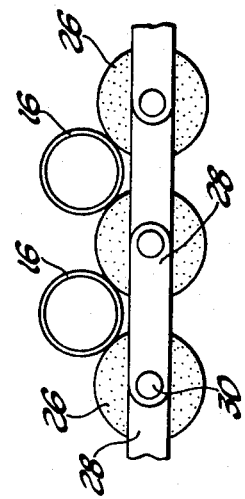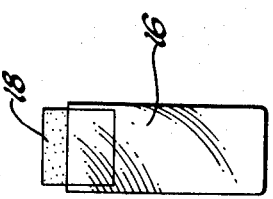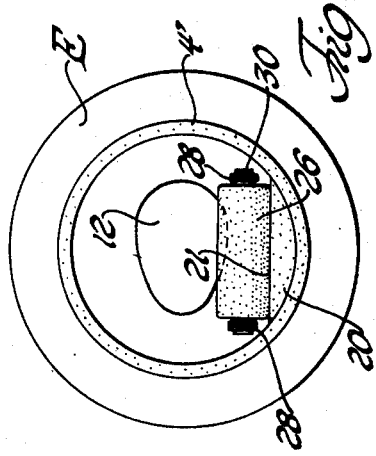

METHOD OF MAGNETICALLY TREATING EGGS AND ANIMAL SEMEN

This is a division of application Ser. No. 403,571, filed Oct. 4, 1973, now U.S. Pat. No. 3,910,233.

This invention relates generally to the treatment of semen to increase the activity of the spermatozoa, and to methods for increasing the production of fertile eggs by fowl, and is particularly concerned with methods and apparatus for increasing the production of fertile eggs by female fowl and increasing the hatch rate of the fertile eggs and the growth rate of the fowl hatched from the eggs by magnetically treating semen from the male fowl as well as the fertile eggs produced by the female fowl inseminated with the treated semen.

Much scientific evidence has been gathered in recent years tending to indicate that magnetism and magnetic energy has a significant influence on biological growth and activity. As discussed in the prior U.S. Pat. No. 3,675,367 and application Ser. No. 268,285 filed July 3, 1973, it has long been known that the rate of germination of seeds and the rate of plant growth from the seeds is affected by magnetism.

It has become a common practice to collect semen from male turkeys, and other fowl, and artificially inseminate the female fowl to obtain the production of fertile eggs. The present invention results from experiments to date by the inventor in the treatment of semen of male turkeys by magnetic energy and the treatment of fertile eggs produced by hens inseminated with the magnetically treated semen.

An important factor that influences the production of fertile eggs from artificially inseminated fowl is the amount and activity of the spermatozoa in the semen with which the female fowl is inseminated. If the number of spermatozoa is low, and the spermatozoa is sluggish, or relatively inactive, there is less likelihood that fertile eggs will be produced. On the other hand, if the spermatozoa is highly active, there is a correspondingly increased likelihood that fertile eggs will be produced by the artificially inseminated female fowl.

Experimentation by the inventor indicates that the spermatozoa in a sample of semen becomes highly active when exposed, under controlled conditions, to a magnetic field such that semen so magnetically treated will tend to significantly increase the number of fertile eggs produced by female fowl inseminated with the magnetically treated semen.

It has further been found by experiments to date by the inventor that the hatch rate of fertile eggs is increased when the eggs are exposed under controlled conditions, to magnetic energy. It is believed that the exposure to magnetic energy has an effect on the RNA (ribonucleic acid) molecule that increases the likelihood of an egg so treated hatching a healthy fowl, and also increases the growth rate of the hatched fowl. Thus, by treating the semen collected from male fowl to increase the energy and activity of the spermatozoa, and then treating the fertile eggs produced thereby, there is a significant increase in the production and quality of the fowl.

It is therefore an object of this invention to provide a method and apparatus for magnetically treating semem from male fowl to increase the production of fertile eggs by female fowl inseminated with the treated semen.

A further object of this invention is to provide a method for magnetically treating fertile eggs produced by female fowl to increase the hatch rate of the fertile eggs and the growth rate of the fowl hatched from the eggs.

A further object is to provide apparatus for magnetically treating eggs, semen collected in vials, or similar containers, by passing the fragile articles through a magnetic field.

Briefly, a method according to the present invention for magnetically treating fertile eggs and animal semen includes placing the eggs or semen into a magnetic field of predetermined intensity to expose the eggs or semen to the magnetic field, and removing the eggs or semen from the magnetic field after a controlled, predetermined period of time. The exposure to the magnetic field apparently induces magnetic energy into the semen or eggs to produce substantially improved results in the production both of the fertile eggs, and the hatch rate of the fertile eggs produced.

It is also believed that the amount of time required to energize the eggs, vials of semen, or other articles by the magnetic field is dependent upon the position of the article in the magnetic field. It is believed that the RNA molecules, for example, of an egg, will orient themselves with the magnetic field, and if in an ideal position with respect to the magnetic field, the energization will take place almost instantaneously. Consequently, the method of the present invention also includes revolving the eggs, or vials of semen, in the magnetic field to constantly change the orientation of the eggs or vials with respect to the magnetic field.

The invention also includes apparatus for carrying out the method of the invention, such apparatus including a magnet for producing a magnetic field, and support means of soft resilient material extending through the magnetic field for supporting the eggs and semen vials as they are moved through the magnetic field for treatment therein.

Other objects, advantages and features of the invention will become apparent from the following description taken in connection with the accompanying drawings in which:

FIG. 2 is a sectional, elevational view of apparatus embodying the invention in another form;

FIG. 3 is a view taken along lines 3-3 of FIG. 2;

FIG. 4 is an elevational view of a vial or container of conventional construction suitable for collecting semen to be treated by the method and apparatus of the invention; and FIG. 5 is a fragmentary elevational view of the conveyor of FIG. 3 with a plurality of vials of the type shown in FIG. 4 supported thereon.

Figure 1:
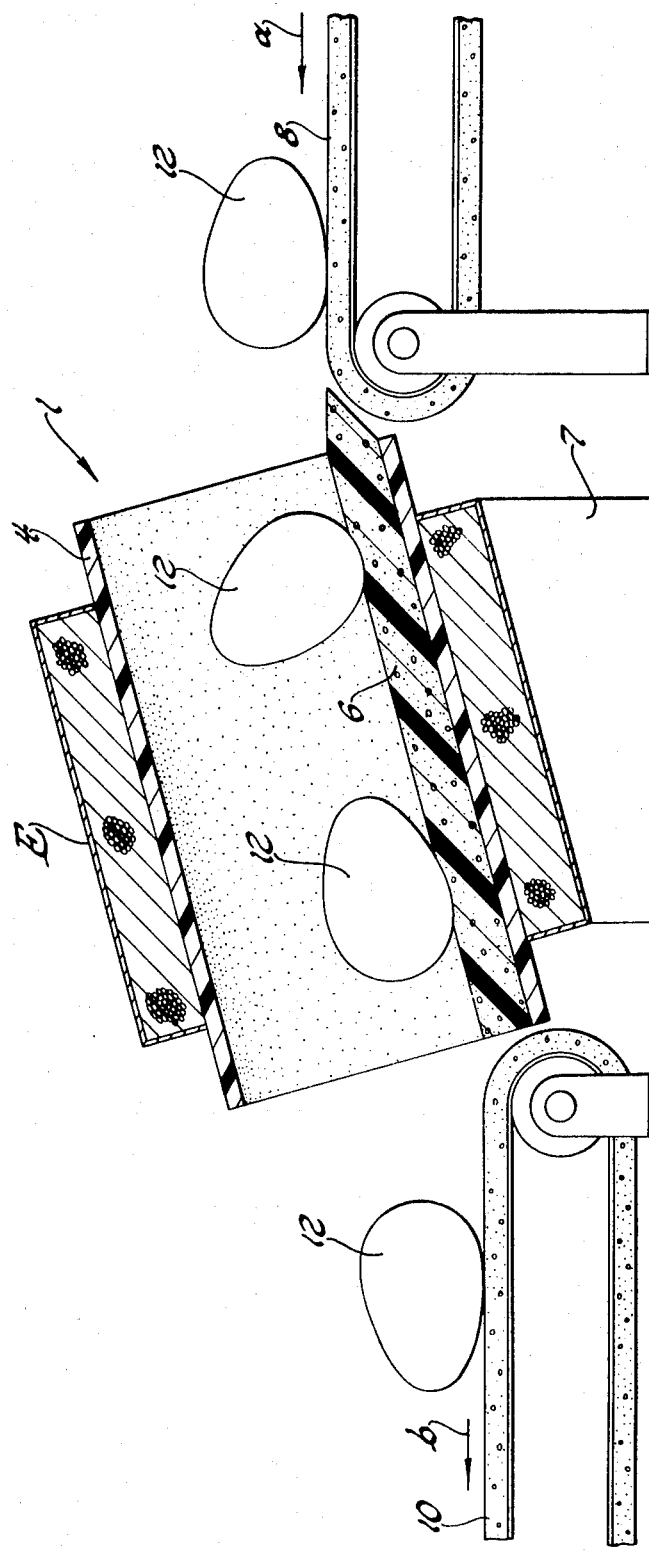
FIG. 1 is a sectional, elevational view of apparatus embodying the invention in one form.

The apparatus shown in FIG. 1 is collectively designated by reference numeral 1 and comprises a magnet E mounted on a tube 4 defining a tubular conduit extending through the magnetic field produced by the magnet E, the tubular conduit 4 having a fixed directional relationship with respect to the magnetic field. Secured to at least a portion of the inner surface of the tubular conduit 4 is a supporting layer 6 of soft, resilient material such as sponge rubber, or the like, for supporting fragile articles moving through the tubular conduit 4, and hence the fielf of the magnet E. The tubular conduit 4 is of nonmagnetic material such as polyvinyl chloride, or material that has little, if any, tendency to become magnetized, and will therefore offer little or no interference to the field of the magnet E. Tube 4 may be of any non-ferrous material such as organic plastic or aluminum.

In the apparatus 1 in FIG. 1, the tube 4 and magnet E are supported on tube supporting means 7 of any conventional construction in an inclined position with the upper end comprising the inlet end of the tubular conduit and the lower end comprising the discharge end of the tubular conduit. Articles are fed to the inlet end of the conduit 4 by a feed conveyor 8 constructed of soft, resilient material such as sponge rubber or the like for handling fragile articles. The direction of feed of the conveyor 8 is indicated by the arrow a.

Articles are conveyed from the lower, discharge end of the tubular conduit 4 and supporting layer 6 by a conveyor 10, also constructed of soft, resilient material such as sponge rubber or the like for handling fragile articles, the conveyor 10 moving the articles in the direction of the arrow b in FIG. 1.

In FIG. 1, the apparatus is shown as magnetically treating eggs which are identified by reference numeral 12. The eggs 12 are conveyed by the conveyor 8 to the upper, inlet end of the tubular member 4 and deposited onto the soft, resilient supporting layer 6. The eggs rolls by gravity over the supporting layer 6 to the lower, discharge end of the conduit 4 where they are received by the discharge conveyor 10. During the time that the eggs are in the conduit 4, they are in the field of the electromagnet E and are exposed to the magnetic field.

The inclination and axial lengths of the magnet E detemines the exposure time of each egg, or vial of semen, in the magnetic field.

FIG. 4 illustrates a vial or container 16 for containing a selected quantity of semen collected from male fowl, the container 16 being of glass, organic plastic or other material that has little, if any, tendency to become magnetized so as to offer no interference to the field of the magnet E. The container 16 includes a cap or closure 18 which may be of any conventional construction such as a cork. The containers 16 may be treated in the apparatus shown in FIG. 1 in the same manner as the eggs 12; that is the containers 16 may be fed into the upper inlet end of the conduit 4 by the feed conveyer 8 and deposited into the upper, inlet end of the tubular conduit 4. The vials 16 will then roll down the surface 6 through the field of the magnet E due to gravity, and will be carried from the lower discharge end of the tubular conduit 4 by conveyor 10.

A second embodiment of the invention is disclosed in FIGS. 2, 3 and 5. The apparatus shown in FIG. 2 is collectively designated by reference numeral 19 and comprises a magnet E mounted on a tube 4' defining a tubular conduit extending through the magnetic field produced by the magnet E, the tubular conduit 4' being of substantially identical construction with the tube 4 of the FIG. 1 embodiment except that a platform 20 having a flat upper surface 21 is provided in the tube 4'. The platform 20 may be of plastic or other non-magnetic material, and may be of either hard plastic, or resilient cellular plastic or sponge rubber or the like.

In the apparatus of FIG. 2, the fragile article support means for supporting eggs 12 or vials 16 comprises an endless conveyor designated collectively by reference numeral 22. The conveyor 22 is supported on sprockets or rollers 24 in such a manner that the upper run of the conveyor extends through the tubular conduit 4'. The conveyor is operable in a manner set forth below to cause articles supported thereby to resolve as the articles are carried by the conveyor through the tubular conduit 4' and magnetic field of the magnet E.

The upper run of the conveyor 22 moves in the direction of arrows c so that the right-hand end, as viewed in FIG. 2, is the inlet end of the conveyor 22, and the lefthand end, as viewed in FIG. 2, is the discharge end of the conveyor 22. Feed and discharge conveyors, such as conveyors 8 and 10 in the embodiment of FIG. 1, may be provided respectively at the inlet and discharge ends of conveyor 22 in FIG. 2.

The conveyor 22 comprises a series of rollers 26 of soft, resilient material such as sponge rubber or the like, the rollers 26 being connected by links 28 connected in end-to-end relationship by pin members 30 extending at least partially through the rollers and defining the axes of the rollers 26. The pin members 30, and hence the axes of the rollers extend transversely to the longitudinal axis of the tubular conduit 4'.

As shown in FIG. 2, the rollers 26 are spaced from each other, and each egg 12 is supported on an adjacent pair of the rollers 26. When the rollers 26 move into engagement with the surface 21 of the platform member 20, the engagement of the periphery of the rollers 26 with the surface 21 causes the rollers 26 to rotate about their respective pin members 30, which motion in turn causes the eggs 12 supported thereby to revolve as the eggs move through the conduit 4' and the field of the magnet E.

The conveyor 22 may be driven in any conventional manner, such as by connecting one of the sprockets or rollers 24 with a power source, and the speed of the conveyor determines the exposure time of each egg 12 in the magnetic field.

FIG. 5 is a fragmentary sectional view of the conveyor 22 illustrating the manner in which the vials 16 are supported on the rollers 26. As the vials 16 enter the field, the engagement of the rollers 26 with the surface 21 of the platform 20 will cause the rollers 26 to rotate about the pin members 30, which rotation in turn will cause the vials 16 to rotate as they move through the magnetic field.

Experimentation to date indicates that the best results are obtained by the method of treatment disclosed herein when the exposure time of the eggs and semen is from three to ten seconds in a magnetic field having an intensity of from 60 to 120 gauss. Based on these test results, therefore, the inclination and length of the tube 4, as well as the axial length of the electromagnet E of FIG. 1 should be such that the eggs roll down the inclined surface of the support surface 6 in from three to ten seconds. Similarly, the speed of the conveyor 22 in the embodiment of FIG. 2 can be controlled to obtain the exposure time of from three to ten seconds of the eggs 12, or vials 16, in the field of the magnet E on the tube 4' of FIG. 2.

The electromagnet E may be of the same construction as disclosed in U.S. Pat. No. 3,675,367, and the intensity of the field may be controlled in the manner disclosed in the latter patent.

As is the case with the tubular conduits 4 and 4', the links 28 and pin members 30 of the conveyor 22 are preferably of material that has little, if any, tendency to become magnetized, and will thus offer little or no interference to the field of magnet E.

The method of treatment of eggs and semen disclosed herein has been tested, and the tests to date indicate significantly increased production of fertile eggs by hens inseminated by semen treated by the method disclosed herein, and indicate significant increases in the hatch rate of eggs produced by the hens. The following are examples of some of the tests run to date with this method.

EXAMPLE I

In this test, semen was collected from male turkeys. The semen was placed in a glass vial and exposed for approximately ten seconds in a magnetic field having an intensity of 100 gauss. The vial was rotated constantly during the time that it was exposed to the magnetic field. A total of 1,840 hens were inseminated over a period of 6 months with the magnetically treated semen, and this group was compared with a control group of 1,840 hens inseminated with untreated semen. The hens inseminated with untreated semen laid 89,263 eggs with 69% of the eggs fertile. The hens inseminated with the magnetically treated semen laid 90,376 eggs with 76.2% of the eggs found to be fertile.

EXAMPLE II

In this test, 48 eggs were each exposed from three to ten seconds to a magnetic field having an intensity of 100 gauss, the eggs being rotated in the magnetic field during the exposure time. The 48 eggs so treated were placed in an incubator with a control group of 48 untreated eggs. 74% of the untreated control group of eggs hatched, while 82% of the treated eggs hatched.

EXAMPLE III

In this test, 246 eggs were treated by the method of this invention and placed in an incubator was 11,700 untreated eggs. The fertility of all of the eggs were found to be 81%. 76% of the treated eggs hatched while only 71% of the untreated eggs hatched. Of the chicks hatched from the two groups, 4.3% of the chicks of the untreated eggs were found to be defective, while only 1.2% of the chicks from the treated eggs were found to be defective, or found to be what is commonly referred to as "crips".

EXAMPLE IV

In this test, 2,440 eggs were selected at random from a group of 12,000 eggs and treated by the method of this invention. All 12,000 eggs were placed in an incubator. The magnetically treated eggs had a hatch rate of 78.1%, while the untreated eggs had a hatch rate of only 71.0%. The chicks from the treated eggs were separated and toe punched for identification. At the time of marketing, the chicks hatched from the treated eggs averaged 0.4 lbs. heavier than the chicks hatched from the untreated eggs.

EXAMPLE V

In this test, 96 eggs having a fertility rate of 89% were divided randomly into two groups of 48 eggs each. One group was magnetically treated by the method disclosed herein. The other groups was not treated. Both groups were placed in the same incubator. The hatch rate of the treated eggs 86% as compared to a hatch rate of 81% of the untreated eggs. The death loss of the chicks up to ten weeks was 1.3% for the chicks hatched from the treated eggs as compared with 8.2% of the chicks hatched from the untreated eggs. All of the chicks were raised in the same pen, and had the same care and feed. The chicks hatched from the magnetically treated eggs were toe punched for identification.

EXAMPLE VI

In this test, out of 12,000 eggs, 2,880 were selected at random and magnetically treated according to the method of this invention. All 12,000 eggs were then placed in an incubator with the treated eggs identified. The hatch rate of the treated eggs was 83% as compared to a hatch rate of 76.4% from the untreated eggs. The death loss of the chicks from the treated eggs was 3.2% as compared with 6.1% of the untreated eggs. The chicks from the treated eggs were marked by toe punching for identification, and the average dressed weight at market of the males hatched from the untreated eggs was 2.9 lbs., and the average dressed weight of the females hatched from the untreated eggs was 2.3 lbs. The average dressed weight of the males hatched from the magnetically treated eggs was 3.4 lbs., and the average dressed weight of the females hatched from the magnetically treated eggs was 3.0 lbs.

EXAMPLE VII

In this test, 12,000 eggs were divided into two equal groups of 6,000 each. One group was magnetically treated according to the method of this invention, and the other group was not treated. 76.1% of the untreated eggs hatched, while 81.2% of the treated eggs hatched. Of the chicks hatched from the treated eggs, 1.0% were rejected as crips, and 3.2% of the chicks from the untreated eggs were rejected as crips. The dressed weight at ten weeks of the males hatched from the untreated eggs averaged 2.9 lbs., while the average dressed weight of the females hatched from the untreated eggs was 2.5 lbs. The average dressed weight of the males hatched from the treated eggs averaged 3.2 lbs., while the average dressed weight of the females hatched from the treated eggs averaged 2.8 lbs. The death loss at 10% of the fowl hatched from the treated eggs was 2.4% as compared with a death loss of the fowl hatched from the untreated eggs of 6.1%, all of the fowl from both groups of eggs having the same care and feeding.

In all of the above tests, as pointed out previously, the exposure time was from 3 to 10 seconds in a magnetic field having an intensity of from 60 to 120 gauss.

While two embodiments of the apparatus are disclosed for carrying out the method disclosed herein, it will be obvious to those skilled in the art that other apparatus for handling fragile articles may be employed to carry the eggs and semen vials through the magnetic field. Various types of apparatus for handling fragile articles may be employed, although, it is believed that such apparatus that does not provide means for rotating and turning the vials and eggs will require that the time of exposure to the magnetic field will be extended. However, the invention is not limited to the specific construction of apparatus disclosed herein, and alterations and variations in the construction and arrangement of parts, all falling within the scope and field of the invention, will be apparent to those skilled in the art.

The embodiments of the invention in which an exclusive property or privilege is claimed are defined as follows:

1. A method of treating male fowl semen to increase the production of fertile eggs by female fowl inseminated with the treated semen comprising: placing a quantity of the semen in a container of non-magnetic material; placing the container in a magnetic field of predetermined intensity to expose the semen to the magnetic field; and then removing the container of semen from the magnetic field after a predetermined period of time; further including the step of revolving the container during the time it is in the magnetic field to constantly change the orientation of the container of semen with respect to the magnetic field during the time that the container is in the magnetic field; wherein the intensity of the magnetic field is about 60 gauss or more, and wherein the predetermined period of time is about 3 seconds or more.

2. A method of treating male fowl semen to increase the production of fertile eggs by female fowl inseminated with the treated semen comprising: placing a quantity of the semen in a container of non-magnetic material; placing the container in a magnetic field of predetermined intensity to expose the semen to the magnetic field; and then removing the container of semen from the magnetic field after a predetermined period of time; and wherein the intensity of the magnetic field is in the range of about 60 to 120 gauss and the period of time is in the range of about 3 to 10 seconds.

3. A method as claimed in claim 2 further including the step of revolving the container during the time it is in the magnetic field to constantly change the orientation of the container of semen with respect to the magnetic field during the time that the container is in the magnetic field.

4. A method of increasing the production of fertile eggs by female fowl and increasing the hatch rate of the fertile eggs and the growth rate of the fowl hatched from the eggs comprising: placing a quantity of male semen in a container of nonmagnetic material; placing the container in a magnetic field of predetermined intensity to expose the semen to the magnetic field; removing the container of semen from the magnetic field after a predetermined period of time; inseminating the female fowl with the magnetically treated semen; and placing fertile eggs produced by the inseminated female fowl in a magnetic field of predetermined intensity for a predetermined period of time; wherein the intensity of the magnetic field is about 60 gauss or more, and wherein the predetermined period of time in the magnetic field for the semen and eggs is about 3 seconds or more.

5. A method as claimed in claim 4 wherein the fertile eggs are placed in said magnetic field for said predetermined period of time prior to incubation.

6. A method as claimed in claim 4 wherein said container of semen is continuously revolved during the time it is in the magnetic field to constantly change the orientation of the container of semen with respect to the magnetic field.

7. A method as claimed in claim 4 wherein the eggs are continuously revolved during the time they are in the magnetic field to constantly change the orientation of the eggs with respect to the magnetic field.

8. A method of increasing the production of fertile eggs by female fowl and increasing the hatch rate of the fertile eggs and the growth rate of the fowl hatched from the eggs comprising: placing a quantity of male semen in a container of nonmagnetic material; placing the container in a magnetic field of predetermined intensity to expose the semen to the magnetic field; removing the container of semen from the magnetic field after a predetermined period of time; inseminating the female fowl with the magnetically treated semen; and placing fertile eggs produced by the inseminated female fowl in a magnetic field of predetermined intensity for a predetermined period of time; wherein the intensity of the magnetic field is about 60 gauss or more, and wherein the predetermined period of time in the magnetic field for the semen and eggs is in the range of about 3 to 10 seconds.

9. A method as claimed in claim 14 wherein the container of semen and the eggs are revolved during the time they are in the magnetic field to change the orientation of the semen and eggs with respect to the magnetic field.

10. A method of treating fertile eggs to increase the hatch rate of the eggs and the growth rate of the fowl hatched from the treated eggs comprising: placing the eggs in a magnetic field of predetermined intensity of about 60 gauss or more to expose the eggs to the magnetic field; and then removing the eggs from the magnetic field after a predetermined period of time in the range of about 3 to 10 seconds.

11. A method of treating semen to increase the activity of the spermatozoa therein comprising: placing a quantity of semen in a container of non-magnetic material; placing the container in a magnetic field of predetermined intensity of about 60 gauss or more to expose the semen to the magnetic field; and then removing the container of semen from the magnetic field after a predetermined period of time of about 3 to 10 seconds.

* * * * *